United States Patent [19]
Gaster

[11] Patent Number: 5,972,935
[45] Date of Patent: Oct. 26, 1999

[54] BIPHENYL(THIO)AMIDE AND BIPENNYLETHAN(THI) ONE DERIVATIVES, THEIR PREPARATION AND THEIR USE AS 5-HT$_{1D}$ RECEPTOR ANTAGONISTS

[75] Inventor: Laramie Mary Gaster, Bishop's Stortford, United Kingdom

[73] Assignee: SmithKline Beecham p.l.c., Brentford, United Kingdom

[21] Appl. No.: 09/011,338

[22] PCT Filed: Aug. 6, 1996

[86] PCT No.: PCT/EP96/03511

§ 371 Date: Apr. 24, 1998

§ 102(e) Date: Apr. 24, 1998

[87] PCT Pub. No.: WO97/07120

PCT Pub. Date: Feb. 27, 1997

[30] Foreign Application Priority Data

Aug. 11, 1995 [GB] United Kingdom .................. 95 16456
Mar. 29, 1996 [GB] United Kingdom .................. 96 06632
Mar. 29, 1996 [GB] United Kingdom .................. 96 06633

[51] Int. Cl.$^6$ ..................... A61K 31/535; A61K 31/44; C07D 413/00; C07D 491/00
[52] U.S. Cl. ................. 514/229.8; 514/291; 514/364; 544/126; 544/142; 546/89; 548/143
[58] Field of Search ..................... 544/126, 142; 514/229.8, 291, 364; 546/89; 548/143

[56] References Cited

FOREIGN PATENT DOCUMENTS

| 2 276 160 | 9/1994 | United Kingdom . |
|---|---|---|
| 2 276 161 | 9/1994 | United Kingdom . |
| 2 276 162 | 9/1994 | United Kingdom . |
| WO 95/15954 | 6/1995 | WIPO . |
| WO 95/17398 | 6/1995 | WIPO . |
| WO 95/17401 | 6/1995 | WIPO . |
| WO 95/30675 | 11/1995 | WIPO . |
| WO 95/32967 | 12/1995 | WIPO . |
| WO 96/06079 | 2/1996 | WIPO . |

OTHER PUBLICATIONS

Clitherow, et al., *J. Med. Chem.*, vol. 37, No. 15, 1994, pp. 2253–2257.
Hartig, et al., *Tips*; vol. 17, No. 3, 1996, pp. 103–105.

Primary Examiner—Deborah C. Lambkin
Attorney, Agent, or Firm—Wayne J. Dustman; William T. King; Charles M. Kinzig

[57] ABSTRACT

The invention relates to novel heterocyclic compounds of formula (I) or a salt or N-oxide thereof, in which R is a group of formulae (i), (ii) or (iii), where $R^1$ is hydrogen, halogen, $C_{1-6}$alkyl, $C_{3-6}$cycloalkyl, $COC_{1-6}$akyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyle, nitro, trifluoromethyl, cyano, $SR^9$, $SOR^9$, $SO_2R^9$, $NR^9CONR^{10}R^{11}$, $NR^{10}SO_2R^{11}$, $SO_2NR^{11}r^{11}$, $SO_2NR^{10}$ $R^{11}$, $CO_2R^{10}$, $CONR^{10}R^{11}$, $CO_2NR^{10}R^{11}$, $CONR^{10}(CH_2)_aCO_2R^{11}$, $(CH_2)_aNR^{10}R^{11}$, $(CH_2)_aCONR^{10}R^{11}$, $(CH_2)_aCOR^{11}$, $(CH_2)_aCO_2C_{1-6}$alkyl, $CO_2(CH_2)_aOR^{10}$, $NR^{10}R^{11}$, $N=CNR^9NR^{10}R^{11}$, $NR^{10}CO(CH_2)_aNR^{10}R^{11}$, $NR^{10}CO_2R^{11}$, $CONHNR^{10}R^{11,CR\ 10}$ $=NOR^{11}$, $CNR^{10}=NOR^{11}$, where $R^9$, $R^{10}$ and $R^{11}$ are independently hydrogen or $C_{1-6}$alkyl and a is 1 to 4; or $R^1$ is a group —X—$R^{12}$ where $R^{12}$ is an optionally substituted 5- to 7-membered heterocyclic ring containing 1 to 4 heteroatoms selected from oxygen, nitrogen or sulphur and X is a bond, O, S, $CH_2$, C=O, $NR^{13}CO$ or $NR^{13}$ where $R^{13}$ is hydrogen or $C_{1-6}$alkyl; $R^4$ and $R^5$ are independently hydrogen, halogen, $C_{1-6}$alkyl, $C_{3-6}$cycloalkyl, $C_{3-6}$cycloalkenyl, $C_{1-6}$alkoxy, hydroxy$C_{1-6}$alkyl, $C_{1-6}$alkyl$OC_{1-6}$alkyl, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are independently hydrogen or $C_{1-6}$alkyl, or $R^4$ and $R^5$ together form a group —$CH_2$)$_r$—$R^{14}$—$(CH_2)_s$— where $R^{14}$ is O, S, $CH_2$ or $NR^{15}$ where $R^{15}$ is hydrogen or $C_{1-6}$alkyl and r and s are independently 0, 1 or 2; $R^2$ is hydrogen, $C_{1-6}$alkyl, optionally substituted aryl or optionally substituted heteroaryl; $R^3$ is hydrogen or $C_{1-6}$alkyl or together with $R^8$ forms a group $(CH_2)_q$ where q is 2, 3 or 4; Z is oxygen or sulphur, p is 1 or 2; P is an optionally substituted bicyclic ring optionally containing one to four heteroatoms; or P is an optionally substituted 5- to 7-membered saturated or partially saturated ring optionally containing one to three heteroatoms; and B is oxygen or sulphur, D is nitrogen, carbon or a CH group; $R^6$ is hydrogen or $C_{1-6}$alkyl and $R^7$ is $C_{1-6}$alkyl, $C_{1-6}$alkoxy or halogen, or $R^6$ together with $R^7$ forms a group —A— where A is $(CR^{16}R^{17})_t$ where t is 1, 2 or 3 and $R^{16}$ and $R^{17}$ are independently hydrogen or $C_{1-6}$alkyl or A is $(CR^{16}R^{17})_u$—J where u is 0, 1, or 2 and J is oxygen, sulphur, $CR^{16}$=$C^{17}$,

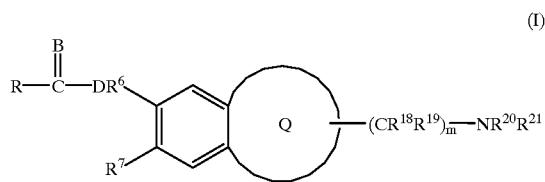

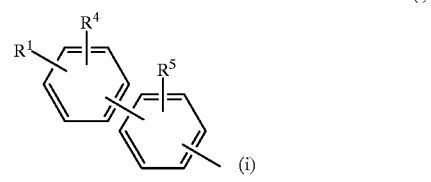

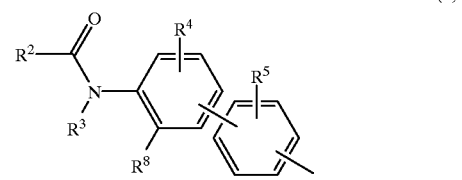

$CR^{16}=N$, $CR^{16}NR^{17}$ or $N=N$; $R^{18}$ and $R^{19}$ are independently hydrogen or $C_{1-6}$alkyl; $R^{20}$ and $R^{21}$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur, m is 0 to 4; and Q is an optionally substituted 5- to 7-membered heterocyclic ring containing 1 to 3 heteroatoms selected from oxygen, nitrogen or sulphur, processes for their preparation, and their use as 5-$HT_{1D}$ receptor antagonists.

12 Claims, No Drawings

BIPHENYL(THIO)AMIDE AND BIPENNYLETHAN(THI) ONE DERIVATIVES, THEIR PREPARATION AND THEIR USE AS 5-HT$_{1D}$ RECEPTOR ANTAGONISTS

The present invention relates to novel heterocyclic compounds, processes for their preparation, and pharmaceutical compositions containing them.

EPA 0 533 266/7/8 disclose a series of benzanilide derivatives which are said to possess 5HT$_{1D}$ receptor antagonist activity. These compounds are said to be of use in the treatment of various CNS disorders. The 5HT$_{1D\beta}$ receptor has now been reclassified as the 5HT$_{1B}$ receptor (P.R Hartig et al Trends in Pharmacological Science, 1996, 17, 103–105.

A structurally distinct class of compounds have now been discovered and have been found to exhibit 5HT$_{1B}$ receptor antagonist activity. In a first aspect, the present invention therefore provides a compound of formula (I) or a salt or N-oxide thereof:

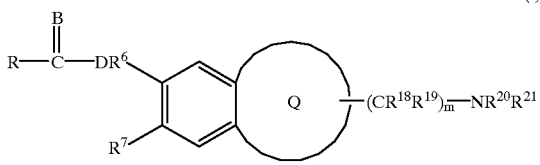

(I)

in which
R is a group of formula (i):

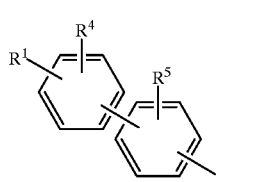

(i)

where
R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, NR$^9$CONR$^{10}$R$^{11}$, NR$^{10}$SO$_2$R$^{11}$, SO$_2$NR$^{10}$R$^{11}$, CO$_2$R$^{10}$, CONR$^{10}$R$^{11}$, CO$_2$NR$^{10}$R$^{11}$, CONR$^{10}$(CH$_2$)$_a$CO$_2$R$^{11}$, (CH$_2$)$_a$NR$^{10}$R$^{11}$, (CH$_2$)$_a$CONR$^{10}$R$^{11}$, (CH$_2$)$_a$NR$^{10}$COR$^{11}$, (CH$_2$)$_a$CO$_2$C$_{1-6}$alkyl, CO$_2$(CH$_2$)$_a$OR$^{10}$, NR$^{10}$R$^{11}$, N=CNR$^9$NR$^{10}$R$^{11}$, NR$^{10}$CO(CH$_2$)$_a$NR$^{10}$R$^{11}$, NR$^{10}$CO$_2$R$^{11}$, CONHNR$^{10}$R$^{11}$, CR10=NOR$^{11}$, CNR$^{10}$=NOR$^{11}$, where R$^9$, R$^{10}$ and R$^{11}$ are independently hydrogen or C$_{1-6}$alkyl and a is 1 to 4; or R$^1$ is a group —X—R$^{12}$ where R$^{12}$ is an optionally substituted 5- to 7-membered heterocyclic ring containing 1 to 4 heteroatoms selected from oxygen, nitrogen or sulphur and X is a bond, O, S, CH$_2$, C=O, NR$^{13}$CO or NR$^{13}$ where R$^{13}$ is hydrogen or C$_{1-6}$alkyl; R$^4$ and R$^5$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl, or R$^4$ and R$^5$ together form a group —(CH$_2$)$_r$—R$^{14}$—(CH$_2$)$_s$— where R$^{14}$ is O, S, CH$_2$ or NR$^{15}$ where R$^{15}$ is hydrogen or C$_{1-6}$alkyl and r and s are independently 0, 1 or 2; or R is a group of formula (ii):

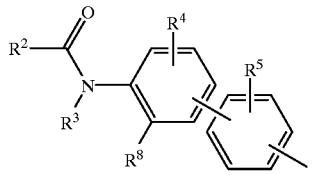

(ii)

where
R$^2$ is hydrogen, C$_{1-6}$alkyl, optionally substituted aryl or optionally substituted heteroaryl;
R$^3$ is hydrogen or C$_{1-6}$alkyl or together with R$^8$ forms a group (CH$_2$)$_q$ where q is 2, 3 or 4; and
R$^4$ and R$^5$ are as defined in formula (i);
or R is a group of formula (iii):

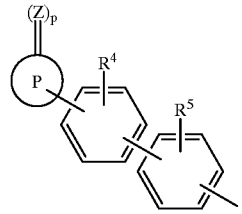

(iii)

where Z is oxygen or sulphur;
p is 1 or 2;
P is an optionally substituted bicyclic ring optionally containing one to four heteroatoms;
or P is an optionally substituted 5- to 7-membered saturated or partially saturated ring optionally containing one to three heteroatoms; and
R$^4$ and R$^5$ are as defined in formula (i);
B is oxygen or sulphur;
D is nitrogen, carbon or a CH group;
R$^6$ is hydrogen or C$_{1-6}$alkyl and R$^7$ is C$_{1-6}$alkyl, C$_{1-6}$alkoxy or halogen, or R$^6$ together with R$^7$ forms a group —A— where A is (CR$^{16}$R$^{17}$)$_t$ where t is 1, 2 or 3 and R$^{16}$ and R$^{17}$ are independently hydrogen or C$_{1-6}$alkyl or A is (CR$^{16}$R$^{17}$)$_u$—J where u is 0, 1 or 2 and J is oxygen, sulphur, CR$^{16}$=CR$^{17}$, CR$^{16}$=N, CR$^{16}$NR$^{17}$ or N=N;
R$^{18}$ and R$^{19}$ are independently hydrogen or C$_{1-6}$alkyl;
R$^{20}$ and R$^{21}$ are independently hydrogen, C$_{1-6}$alkyl, aralkyl, or together with the nitrogen atom to which they are attached form an optionally substituted 5- to 7-membered heterocyclic ring containing one or two heteroatoms selected from oxygen; nitrogen or sulphur;
m is 0 to 4; and
Q is an optionally substituted 5 to 7-membered heterocyclic ring containing 1 to 3 heteroatoms selected from oxygen, nitrogen or sulphur.

C$_{1-6}$alkyl groups, whether alone or as part of another group, may be straight chain or branched. As used herein the term aryl includes phenyl. Heteroaryl groups include thienyl, furyl, pyridyl, pyrimidyl and pyrazinyl groups. Optional substituents for aryl and heteroaryl groups include $C_{1-6}$alkyl such as methyl.

Suitably R is a group of formula (i), (ii) or (iii) as defined above. Preferably R is a group of formula (i) where $R^1$ is preferably a group —X—$R^{12}$. Preferably X is a bond. Examples of $R^{12}$ groups include thienyl, furyl, pyrrolyl, triazolyl, diazolyl, imidazolyl, oxazolyl, thiazyl, oxadiazolyl, isothiazolyl, isoxazolyl, thiadiazolyl, pyridyl, pyrimidyl and pyrazinyl. The heterocyclic rings can be linked to the remainder of the molecule via a carbon atom or, when present, a nitrogen atom. Suitable substituents for these rings include those $R^1$ groups as defined above. Preferably $R^{12}$ is optionally substituted oxadiazolyl. Preferred substituents for such oxadiazolyl groups include $C_{1-6}$alkyl such as methyl or ethyl, and $NR^{10}R^{11}$ as defined above. Most preferably $R^{12}$ is a 5-methyl-1,2,4-oxadiazol-3-yl.

When R is a group of formula (ii) preferred groups include those where $R^2$ is $C_{1-6}$alkyl, for example methyl, and $R^3$ and $R^8$ form a $(CH_2)_3$ group When R is a group of formula (iii) as defined above P is preferably an optionally substituted 5- to 7-membered saturated or partially saturated ring optionally containing one or two heteroatoms. Preferably Z is oxygen and p is 1. More preferably P is a lactam ring of formula (a):

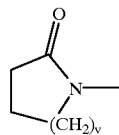

(a)

where v is 1, 2 or 3. Preferably v is 1 or 2, forming a 5- or 6-membered ring. Other preferred R groups include bicyclic rings of formula (b):

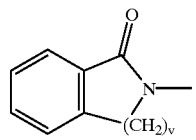

(b)

where v is 1 or 2.

Suitably $R^4$ and $R^5$ are independently hydrogen, halogen, $C_{1-6}$alkyl, $C_{3-6}$cycloalkyl, $C_{3-6}$cycloalkenyl, $C_{1-6}$alkoxy, hydroxy$C_{1-6}$alkyl, $C_{1-6}$alkylOC$_{1-6}$alkyl, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are independently hydrogen or $C_{1-6}$alkyl, or $R^4$ and $R^5$ together form a group —$(CH_2)_r$—$R^{14}$—$(CH_2)_s$— where $R^{14}$ is O, S, $CH_2$ or $NR^{15}$ where $R^{15}$ is hydrogen or $C_{1-6}$alkyl and r and s are independently 0, 1 or 2.

Preferably $R^4$ is $C_{1-6}$alkyl, in particular methyl. Preferably $R^5$ is hydrogen.

Suitably B is oxygen or sulphur. Preferably B is oxygen.

Suitably D is nitrogen, carbon or a CH group. Preferably D is nitrogen.

Suitably $R^6$ is hydrogen or $C_{1-6}$alkyl and $R^7$ is $C_{1-6}$alkoxy or halogen, or $R^6$ together with $R^7$ forms a group —A— where A is $(CR^{16}R^{17})_t$ where t is 1, 2 or 3 and $R^{16}$ and $R^{17}$ are independently hydrogen or $C_{1-6}$alkyl or A is $(CR^{16}R^{17})_u$ —J where u is 0, 1 or 2 and J is oxygen, sulphur, $CR^{16}$=$CR^{17}$, $CR^{16}$=N, $CR^{16}NR^{17}$ or N=N. Preferably $R^6$ together with $R^7$ forms a group —A— where A is $(CR^{16}R^{17})_t$ where t is 2 or 3 and $R^{16}$ and $R^{17}$ are both hydrogen.

Suitably $R^{18}$ and $R^{19}$ are independently hydrogen or $C_{1-6}$alkyl. Preferably $R^{18}$ and $R^{19}$ are both hydrogen. Suitably m is 0 to 4. preferably m is 2.

Suitably $R^{20}$ and $R^{21}$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur. Examples of $R^{20}$ and $R^{21}$ as heterocyclic rings include pyrrolidine, morpholine, piperazine and piperidine. Optional substituents for such rings include $C_{1-6}$alkyl. Preferably $R^{20}$ and $R^{21}$ are both $C_{1-16}$alkyl, in particular methyl.

Suitably Q is an optionally substituted 5 to 7-membered heterocyclic ring containing 1 to 3 heteroatoms selected from oxygen, nitrogen or sulphur. Preferably Q is a 5- or 6-membered ring containing one or two heteroatoms. More preferably Q is a saturated ring containing two heteroatoms, in particular nitrogen and oxygen. Most preferably Q is a morpholine ring substituted on the nitrogen atom by the group —$(CR^{18}R^{19})_m$—$NR^{20}R^{21}$.

Particularly preferred compounds of the invention include: 4-(2-Dimethylaminoethyl)-2,3,6,7,8,9-hexahydro-6-{2'-methyl-4'-(5-methyl-1,2,4-oxadiazol-3-yl)biphenyl-4-carbonyl}-4H-pyrido[2,3-g][1,4]benzoxazine, 2-(N,N-Dimethyl-3,4,6,7,8,9-hexahydro-6-[2'-methyl-4'-(5-methyl-1,2,4-oxadiazol-3-yl)biphenyl-4-carbonyl]-2H-pyrano[2,3-g]quinolin-4-yl)ethanamine, 2-(N,N-Dimethyl-2,3,5,6,7,8-hexahydro-5-[2'-methyl-4'-(5-methyl-1,2,4-oxadiazol-3-yl) biphenyl-4-carbonyl]furo[2,3-g]quinolin-3-yl)ethanamine, 4(2-Dimethylaminoethyl)-2,3,4,6,7,8-hexahydro-6-[2'-methyl-4'-(5-methyl-1,2,4-oxadiazol-3-yl)biphenyl-4-carbonyl]pyrrolo [2,3-g][1,4]benzoxazine, 3-(2-Dimethylaminoethyl)-5-[2'-methyl-4'-(5-methyl-1,2,4-oxadiazol-3-yl)biphenyl4-carbonyl]-2,3,6,7-tetrahydrofuro [2,3-f]indole, 4-(2-Dimethylaminoethyl)-2,3,6,7,8,9-hexahydro-6-[2'-methyl4'-(2-oxopyrrolidin-1-yl)biphenyl-4-carbonyl]-4H-pyrido[2,3-g][1,4]benzoxazine, or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises.

(a) for compunds of formula (I) where D is nitrogen and B is oxygen, reaction of a compound of formula (II):

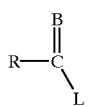

(II)

in which R is as as defined in formula (I), B is oxygen and L is a leaving group. with a compound of formula (III):

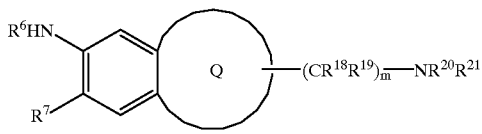

(III)

wherein $R^6$, $R^7$, $R^{18}R^{19}$, $R^{20}$, $R^{21}$, Q and m are as defined in formula (I) and optionally thereafter in any order:
converting a compound of formula (I) into another compound of formula (I)
forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazide. Preferably the group L is halo, particularly chloro.

A compound of formulae (II) and (III) are typically reacted together in an inert organic solvent such as DMF, THF or dichloromethane at ambient or elevated temperature in the presence of a base such as an alkali metal hydroxide, triethylamine or pyridine.

Intermediate compounds of formulae (II) can be prepared using standard procedures including the techniques disclosed in EPA 533266/7/8. Compounds of formula (III) can be prepared using standard chemistry. Certain intermediate compounds of formula (II) and (III) are novel and form a further aspect of the invention.

Alternatively compounds of formula (II) can be reacted with compounds of formula (III) where L is an ester forming group in the presence of an organo-aluminium reagent such as trimethylaluminium. Such a reaction is typically carried out in the presence of an inert solvent such as toluene.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

$5HT_{1B}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include motor disorders such as Parkinson's disease, dementia in Parkinson's disease, neuroleptic-induced Parkinsonism and tardive dyskinesias, as well as other psychiatric disorders.

$5HT_{1B}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

Description 1

4-(2-Dimethylaminoethyl)-6-nitro-2H-1,4-benzoxazin-3(4H)-one

To a suspension of 6-nitro-2H-1,4-benzoxazin-3(4H)-one (J. Med. Chem. 1989, 32, 1627–1630) (1 g, 5.7 mmol) in dry THF (20 ml) at 0° C. under argon, was added NaH (0.16 g, 5.7 mmol, 80% dispersion in mineral oil). A solution of 2-dimethylaminoethyl chloride (2.3 g, 20.8 mmol) in dry toluene (15 ml) was added and the reaction mixture heated under reflux for 19 hr. After cooling, water was added dropwise until effervescence had ceased, then the mixture was separated and the aqueous further extracted with EtOAc. The organic layers were combined, dried ($Na_2SO_4$) and evaporated under reduced pressure to give a pale brown solid (1.08 g, 79%).

$^1$H NMR (250 MHz, $CDCl_3$) δ: 8.03 (d, 1H), 7.94 (dd, 1H), 7.04 (d, 1H), 4.73 (s,2 H), 4.11 (t, 2H) 2.6 (t, 2H), 2.35 (s, 6H).

Description 2

3,4-Dihydro4-(2-dimethylaminoethyl)-6-nitro-2H-1,4-benzoxazine

Boron trifluoride etherate (2 ml, 16.2 mmol) was added dropwise to a suspension of sodium borohydride (0.46 g, 12 mmol) in dry THF (30 ml) at 0° C., under argon. After 1 hr, a solution of 4-(2- dimethylaminoethyl)-6-nitro-2H-1,4-benzoxazine-3(4H )-one (D1, 1.08 g, 4 mmol) in dry THF (20 ml) was added. The reaction mixture was heated under reflux for 2 hr, then cooled in ice. Aqueous $NaHCO_3$ was added dropwise until effervescence ceased, then the solvent was removed under reduced pressure and the residue dissolved in a mixture of EtOH (10 ml) and 5N HCl (10 ml) and heated under reflux for 45 minutes. After cooling, the solvent was removed under reduced pressure. The residue was treated with satturated $K_2CO_3$ solution to pH 8, then extracted with EtOAc. The combined extracts were dried ($Na_2SO_4$) and evaporated under reduced pressure to give the title compound (0.94 g, 92%).

$^1$H NMR (200 MHz, $CDC_3$) δ: 7.52 (m, 2H) 6.78 (d, 1H), 4.30 (t, 2H), 3.42 (m, 4H), 2.56 (t, 2H), 2.31 (s, 6H)

Description 3

6-Amino-3,4-dihydro-4-(2-dimethylaminoethyl)-2H-1,4-benzoxazine

A stirred suspension of 3,4-dihydro-4-(2-dimethylamninoethyl)-6-nitro-2H-1,4-benzoxazine (D2, 0.94 g, 0.004 mol) in ethanol (10 ml) was hydrogenated over 10% Pd-C (0.2 g) at atmospheric pressure and temperature until uptake of hydrogen ceased (2 h). The catalyst was removed by filtration through kieselguhr and the filtrate concentrated in vacuo to afford the title compound as a brown oil (0.84 g, 100%).

$^1$H NMR (200 MHz, $CDC_3$) δ: 6.58(d, 1H), 6.08(d, 1H), 5.98 (dd, 1H), 4.13 (t, 2H), 3.35 (m, 6H), 2.50 (t, 2H), 2.30 (s, 6H).

Description 4

2,3-Dihydro4-(2-dimethylaminoethyl)-4H-pyrido[2,3-g][1,4]benzoxazine

6-Amino-3,4-dihydro-4-(2-dimethylaminoethyl)-2H-1,4-benzoxazine (D3, 4.66 g, 21 mmol), glycerol (2.9 g, 31 mmol) and iodine (0.135 g, 0.5 mmol) were stirred as conc. $H_2SO_4$ (3.2 ml, 60 mmol) was cautiously added. The mixture was stirred at 180° C. for 2 h, cooled, dispersed in water (300 ml), basified (40% NaOH), and extracted with dichloromethane. The extract was dried ($Na_2SO_4$) and evaporated to an oil, which was chromatographed on silica, eluting with 20% methanol/dichloromethane. This gave the title compound (0.50 g, 9%) as a dark oil.

$^1$H NMR (200 MHz, $CDC_3$) δ: 8.61 (dd, 1H), 7.85 (d, 1H), 7.0–7.15 (m, 3H), 4.31 (t, 2H), 3.58 (m, 4H), 2.65 (t, 2H), 2.33 (s, 6H).

Description 5

4-(2-Dimethylaminoethyl)-2,3,6,7,8,9-hexahydro-4-pyrido[2,3-g][1,4]benzoxazine 2,3-Dihydro-4-(2-dimethylaminoethyl)-4H-pyrido[2,3-g][1,4]benzoxazine (D4, 0.53 g, 2 mmol) and platinum dioxide (0.25 g, 1.1 mmol) were hydrogenated at 50 psi $H_2$ in 5% acetic acid/ethanol (50 ml) for 2 h. Catalyst was filtered off onto kieselgular, and the filtrate was evaporated to dryness, dissolved in dichloromethane, washed with $NaHCO_3$ solution, dried ($Na_2SO_4$) and evaporated to give the title compound (0.29 g, 53%) as a dark oil.

$^1$H NMR (250 MHz, $CDCl_3$) δ: 6.43 (s, 1H), 6.02 (s, 1H), 4.15 (m, 2H), 3.2–3.4 (m, 6H), 2.63 (t, 2H), 2.51 (q, 2H), 2.30 (s, 3H), 2.28 (s, 3H), 1.90 (m, 2H).

Description 6

6-Nitrochroman-4-acetic acid and 8-nitrochroman-4-acetic acid

Chroman-4-acetic acid (4.32 g, 22 mmol) was stirred in acetic anhydride (50 ml), standing in a cool water-bath, as copper (II) nitrate trihydrate (6.6 g, 27 mmol) was added over 0.5 h.

After stirring for 16 h, the mixture was poured into water and extracted with ethyl acetate. The extract was dried ($Na_2SO_4$) and evaporated to give a mixture of the title compounds (3.92 g, 73%), in approximate proportions 2(6-nitro):3(8-nitro), together with some 6,8-dinitro compound.

$^1$H NMR (250 MHz, $CDCl_3$) δ (ppm): 8.13 (d, 6-$NO_2$, 1H), 8.04 (dd, 6—$NO_2$, 1H, 7.70 (d, 8-$NO_2$, 1H), 7.38 (d, 8-$NO_2$, 1H), 6.92 (m, both, 1H), 4.35 (m, both, 2H), 3.45 (m, both, 2H) 2.6–3.0 (2xABq, both, 2H), 2.30 (m, both, 1H), 2.05 (m, both, 1H).

Description 7

N,N-Dimethyl-6-nitrochroman-4-acetamide and N,N-dimethyl-8-nitrochroman-4-acetamide The mixture of 6- and 8-nitrochroman-4-acetic acids (D6, 3.39 g, 14 mmol) was stirred at reflux in thionyl chloride (50 ml) for 0.75 h, cooled, and evaporated to give an oil. This was dissolved in dichloromethane, and stirred vigorously with dimethylamine (40% aq. solution, 10 ml) for 0.5 h. After separation, the organic portion was washed with $K_2CO_3$ solution, dried ($Na_2SO_4$) and evaporated to the mixture of title compounds (2:3 mixture, as before) as a dark brown oil (3.54 g, 94%).

$^1$H NMR (250 MHz, $CDCl_3$) δ (ppm): 8.09 (d, 6-$NO_2$, 1H), 8.01 (dd, 6-$NO_2$, 1H), 7.67 (d, 8-$NO_2$, 1H), 7.37 (d, 8-$NO_2$, 1H), 6.90 (t, 8-$NO_2$, 1H), 6.88 (d, 6-$NO_2$, 1H), 4.2–4.55 (m, both, 2H), 3.6 (m, both, 1H), 3.0 (2xd, both, 6H), 2.5–2.85 (m, both, 2H), 2.25 (m, both, 1H), 1.95 (m, both, 1H).

Description 8

6-Amino-N,N-dimethylchroman-4-acetamide

This was prepared from the mixture of N,N-dimethyl-6- and -8-nitrochroman-4-acetamides (D7, 3.54 g, 13 mmol), following the procedure of Description 3, but using 1:1 acetic acid/ethanol as solvent. Neutralisation of the crude product, followed by chromatography on silica, eluting with 0–4% methanol/dichloromethane, gave the pure title compound (0.49 g, 12%) in addition to the pure 8-amino compound (1.38 g, 34%).

$^1$H NMR (200 MHz, $CDCl_3$) δ (ppm): 6.63 (d, 1H), 6.5 (m, 2H), 4.1 (m, 2H), 3.4 (m, 3H), 2.99 (s, 3H), 2.97 (s, 3H), 2.5–2.8 (Abq, 2H), 2.2 (m, 1H), 1.8 (m, 1H).

Description 9

2-(6-Amino4-chromanyl)-N,N-dimethylethylamine

6-Amino-N,N-dimethylchroman-4-acetamide (D8, 0.49 g, 2.1 mmol) was dissolved under Ar in dry THF (20 ml), and added to a stirred suspension of lithium aluminium hydride (0.16 g, 4.2 mmol) in dry THF (2 ml ). The mixture wa s stirred at reflux for 3 h, cooled, and treated successively with water (0.16 ml), 10% NaOH (0.16 ml) and water (0.48 ml) The solid was filtered off, and the filtrate was evaporated to give the title compound (0.41 g, 97%) as a red oil.

$^1$ H NMR (250 MHz, $CDCl_3$) δ (ppm): 6.63 (d, 1H), 6.5 (m, 2H), 4.1 (m, 2H), 3.35 (b, 2H), 2.7 (m, 1H), 2.35 (m, 2H), 2.26 (s, 6H), 2.0 (m, 2H), 1.75 (m, 2H).

Description 10

2-(3,4-Dihydro-N,N-dimethyl-2H-pyrano[2,3-g]quinolin-4-yl) ethanamine

This was prepared from 2-(6-amino-4-chromanyl)-N,N-dimethylethylamine (D9, 0.41 g, 1.9 mmol) following the procedure of Description 4. Chromatography on silica, eluting with 0–25% methanol/dichloromethane, gave the title compound (84 mg, 18%) as aplight yellow gum.

$^1$H NMR (250 MHz, $CDCl_3$) δ (ppm): 8.72 (1H, m), 7.98 (1H, d), 7.91 (1H, s), 7.26 (dd 1H), 7.13 (t, 1H), 4.3 (m, 2H), 3.2 (m, 1H), 2.45 (m, 2H), 2.30 (s, 6H), 2.17 (m, 2H), 1.75–1.95 (m, 2H).

Description 11

2-(N,N-Dimethyl-3,4,6,7,8,9-hexahydro-2H-pyrano[2,3-g]quinolin-4-yl)ethanamine

This was prepared from 2-(3,4-dihydro-N,N-dimethyl-2H-pyrano[2,3-g]quinoline-4-yl)ethanamide (D10, 84 mg, 0.33 mmol) following the procedure of Description 5. This gave the title compound (90 mg, quantitative) as a pale green oil.

$^1$H NMR (250 MHz, $CDCl_3$) δ (ppm): 6.45 (s, 1H), 6.32 (s, 1H), 4.95 (b, 1H), 4.10 (m, 2H), 3.24 (t, 2H), 2.77 (m, 1H), 2.72 (t, 2H), 2.50 (t, 2H), 2.32 (s, 6H), 1.85–2.1 (m, 4H), 1.65–1.8 (m, 2H).

Description 12

2,3-Dihydro-N,N-dimethyl-5-nitrobenzofuran-3-acetamide

This was prepared from 2,3-dihydro-5-nitrobenzofiiran-3-acetic acid, following the procedure of Description 7. This gave the title compound (94%) as a ye llow solid.

$^1$H NMR (200 MHz, $CDCl_3$) δ (ppm): 8.1 (m, 2H), 6.82 (d, 1H), 5.06 (t, 1H), 4.40 (dd, 1H), 4.03 (m, 1H), 3.01 (s, 3H), 2.99 (s, 3H), 2.5–3.0 (Abq, 2H).

Description 13

5-Amino-2,3-dihydro-N,N-dimethylbenzofuran-3-acetamide

This was prepared from 2,3-dihydro-N,N-dimethyl-5-nitrobenzofuran-3-acetamide (D12), following the procedure of Description 3. This gave the title compound as a brown oil.

$^1$H NMR (200 MHz, $CDCl_3$) δ (ppm): 6.6 (m, 2H), 6.49 (dd, 1H), 4.76 (t, 1H), 4.15 (dd, 1H), 3.88 (m, 1H), 3.40 (bs, 2H), 2.99 (s, 3H), 2.97 (s, 3H), 2.45–2.85 (Abq, 2H).

Description 14

2-(5-Amino-2,3-dihydro-N,N-dimethylbenzofuran-3-yl)ethanamine

This was prepared from 5-amino-2,3-dihydro-N,N-dimethylbenzofuran-3-acetamide (D13), following the procedure of Description 9. This gave the title compound (66%) as a brown oil.

$^1$H NMR (250 MHz, $CDCl_3$) δ (ppm): 6.58 (m, 2H), 6.48 (dd, 1H), 4.59 (t, 1H), 4.16 (dd, 1H), 3.40 (m, 3H), 2.33 (m, 1H), 2.24 (s, 6H), 1.92 (m, 1H), 1.52 (m, 2H).

Description 15

2,3-Dihydro-3-(2-dimethylaminoethyl)furo[2,3-g]quinoline

This was prepared from 2-(5-amino-2,3-dihydro-N,N-dimethylbenzoforan-3-yl)ethanamine (DS14), following the procedure of Description 4. This gave the title compound (47%) as a dark oil.

¹H NMR (250 MHz, CDCl₃) δ (ppm): 8.70 (m, 2H), 7.98 (d, 1H), 7.86 (s, 1H), 7.29 (dd, 1H), 7.03 (s, 1H), 4.79 (t, 1H), 4.34 (dd, 1H), 3.70 (m, 3H), 2.4 (m, 2H), 2.24 (s, 6H), 1.8–2.2 (m, 2H).

Description 16

3-(2-Dimethylaminoethyl)-2,3,5,6,7,8-hexahydrofuro[2,3-g]quinoline

This was prepared from 2,3-dihydro-3-(2-dimethylaminoethyl)furo[2,3-g]quinoline (D15), following the procedure of Description 5. This gave the title compound (78%) as a dark oil.

¹H NMR (200 MHz) δ (ppm): 6.44 (s, 1H), 6.38 (s, 1H), 4.54 (t, 1H), 4.12 (dd, 1H), 3.36 (m, 1H), 3.25 (t, 2H), 3.05 (b, 1H), 2.73 (t, 2H), 2.2–2.4 (m, 2H), 2.23 (s, 6H), 1.90 (m, 3H), 1.7 (m, 1H).

Description 17

3,4-Dihydro-6-(2,2-dimethoxyethyl)amino-4-(2-dimethylaminoethyl)-2H-1,4-benzoxazine 6-Amino-3,4-dihydro-4-(2-dimethylaminoethyl)-2H-1,4-benzoxazine (D3, 1.78 g, 8.1 mmol) and dimethoxyacetaldehyde (40% in MTBE, 3.1 g) were hydrogenated over 10% palladium on carbon (0.5g) in ethanol (70 ml) for 24 h. The catalyst was filtered off, and the filtrate was evaporated to dryness. The residue was dissolved in ethyl acetate, washed with water and brine, dried (Na₂SO₄) and evaporated to give the title compound (1.92 g, 77%) as a brown oil.

¹H NMR (200 MHz, CDCl₃) δ (ppm): 6.62 (d, 1H), 6.03 (d, 1H), 5.93 (dd, 1H), 4.58 (t, 1H), 4.16 (t, 2H), 3.41 (s, 6H), 3.3–3.5 (m, 5H), 3.19 (d, 2H), 2.50 (t, 2H, 2.29 (s, 6H).

Description 18

4-(2-Dimethylaminoethyl)-2,3,4,6-tetrahydropyrrolo[2,3-g]benzoxazine 3,4-Dihydro-6-(2,2-dimethoxyethyl)amino-4-(2-dimethylaminoethyl)-2H-1,4-benzoxazine (D17, 0.65 g, 2.1 mmol) was stirred under Ar in trifluoroacetic acid (TFA, 2.7 ml) at 0° C. as trifluoroacetic anhydride (2.7 ml) was added dropwise. The mixture was stirred at 0° C. for 40 min, diluted with TFA (3.9 ml), and then stirred at reflux for 4 h. Solvent was removed in vacuo, and the residue was purified by chromatography on silica, eluting with 10% methanol/dichloromethane. This gave the title compound (42 mg, 8%) as a dark green gum.

¹H NMR (200 MHz, CDCl₃) δ (ppm): 7.88 (b s, 1H), 7.00 (s, 1H), 6.98 (m, 1H), 6.64 (s, 1H), 6.33 (m, 1H), 4.22 (t, 2H), 3.44 (t, 2H), 3.40 (t, 2H), 2.56 (t, 2H), 2.32 (s, 6H).

Description 19

4-(2-Dimethylaminoethyl)-2,3,4,6,7,8-hexahydropyrrolo[2,3-g][1,4]benzoxazine 4-(2-Dimethylaminoethyl)-2,3,4,6-tetrahydropyrrolo[2,3-g][1,4]benzoxazine (D18, 42 mg, 0.17 mmol) was stirred in acetic acid (5 ml) as sodium cyanoborohydride (33 mg, 0.52 mmol) was added portionwise over 10 min. The mixture was stirred for 2 h, diluted with water, basified with potassium carbonate, and extracted with ethyl acetate. The extract was dried (Na₂SO₄) and evaporated to give the title compound (34 mg, 80%) as a green gum.

¹H NMR (200 MHz, CDCl₃) δ (ppm): 6.60 (s, 1H), 6.12 (s, 1H), 4.13 (t, 2H), 3.6 (m, 3H), 3.49 (t, 2H), 3.34 (m, 2H), 2.92 (t, 2H), 2.60 (t, 2H), 2.37 (s, 6H).

Description 20

Methyl 4-[(1-acetyl-6-bromoindolin-5-yl)oxy] crotonate

1-Acetyl-6-bromo-5-hydroxyindoline (Tetrahedron, 1973, 29 (8), 1115) (2.54 g, 10 mmol) was stirred under Ar in dry DMF (50 ml) as sodium hydride (80%, 0.33 g, 11 mmol) was added over 10 min. After a further 10 min, methyl 4-bromocrotonate (1.75 ml, 15 mmol) was added. The mixture was stirred at 60° C. for 2 h, cooled, and diluted with water. The precipitated material was filtered off and washed with water and ether, affording the title compound (2.40 g, 68%) as a brown solid. NMR showed a mixture of isomers (ca. 1:1).

¹H NMR (200 MHz, CDCl₃) δ (ppm): 8.45 (s, 1H), 7.12 (t) and 7.04 (t) (1 H), 6.72 (s, 1H), 6.37 (t) and 6.28 (t) (1H), 4.72 (m, 2H), 4.08 (t, 2H), 3.76 (s, 3H), 3.13 (t, 2H), 2.20 (s, 3H).

Description 21

Methyl 5-acetyl-2,3,6,7-tetrahydrofuro[2,3-f]indol-3-ylacetate

Methyl 4-[(1-acetyl-6-bromoindolin-5-yl)oxy]crotonate (D20, 2.40 g, 6.8 mmol) and AIBN (0.03 g) were stirred under Ar at reflux in benzene (60 ml) as tri-n-butyltin hydride (2.73 ml, 10.1 mmol) was added dropwise in benzene (30 ml) over 1 h. The mixture was stirred at reflux for 42 h, and evaporated to dryness. Reaction being incomplete, this was treated again as above, reacting for a fuirther 24 h, and then again evaporating to dryness.

Chromatography on silica, eluting with ethyl acetate, gave the title compound (1.04 g, 58%) as a pale yellow solid.

¹H NMR (200 MHz, CDCl₃) δ (ppm): 8.06 (s, 1H), 6.62 (s, 1H), 4.77 (t, 1H), 4.27 (dd, 1H), 4.04 (t, 2H), 3.83 (m, 1H), 3.72 (s, 3H), 3.13 (t, 2H), 2.86 (dd, 1H), 2.54 H,(dd, 1H), 2.20 (s, 3H).

Description 22

5-(Benzyloxycarbonyl)-2,3,6,7-tetrahydrofuro[2,3-f] indol-3-yl acetic acid

Methyl 5-acetyl-2,3,6,7-tetrahydrofuro[2,3-f]lindol-3-ylacetate (D21, 1.04 g, 4.0 mmol) was stirred at reflux under Ar in 5M HCl for 6 h, and evaporated to dryness. The residue was stirred in 2.5M NaOH (40 ml) at 0° C. and treated with benzyl chloroformate (1.38 ml, 8.0 mmol). The mixture was stirred vigorously for 2.5 h, washed with ether, acidified (5M HCl), and extracted with ethyl acetate. The extract was dried (Na₂SO₄) and evaporated to give the title compound (1.09 g, 77%) as a brown solid.

¹H NMR (200 MHz, CDC₃) δ (ppm): 7.75 (s, 1H), 7.38 (s, 5H), 6.62 (s, 1H), 5.26 (s, 2H), 4.77 (t, 1H), 4.29 (m, 1H), 4.07 (t, 2H), 3.82 (m, 1H), 3.08 (t, 2H), 2.5–3.0 H (m, 2H).

Description 23

5-(Benzyloxycarbonyl)-N,N-dimethyl-2,3,6,7-tetrahydrofuro[2,3-f]indol-3-ylacetamide 5-(Benzyloxycarbonyl)-2,3,6,7-tetrahydrofuro[2,3-f] indol-3-ylacetic acid (D22, 0.89 g, 2.5 mmol) and triethylamine (0.7 ml, 5 mmol) were stirred in dichloromethane (80 ml) under Ar at 0° C. as ethyl chloroformate (0.27 ml, 92.8 mmol) was added. The mixture was stirred for 2 h, and dimethylamine gas was then bubbled through the solution for 10 min. It was then washed with water, $K_2CO_3$ solution and brine, dried ($Na_2SO_4$) and evaporated. Chromatography of the crude product on silica, eluting with 75% ethyl acetate/petroleum ether (b.p. 60–80° C.) gave the title compound (0.44 g, 46%) as an off-white solid.

$^1$H NMR (200 MHz, $CDCl_3$) δ (ppm): 7.73 (s, 1H), 7.35 (m, 5H), 6.62 (s, 1H), 5.25 (s, 2H), 4.90 (t, 1H), 4.23 (dd, 1H), 4.08 (t, 2H), 3.87 (m, 1H), 3.08 (t, 2H), 2.96 (s, 6H), 2.92 (m, 1H), 2.51 (dd, 1H).

Description 24

N,N-Dimethyl-2,3,6,7-tetrahydrofuro[2,3-f]indol-3-ylacetamide

This was prepared from 5-(benzyloxycarbonyl)-N,N-dimethyl-2,3,6,7-tetrahydrofuro[2,3-5 f]indol-3-ylacetamide (D23), following the procedure of Description 3. The product was contaminated with a little of the corresponding indole; reduction following the procedure of Description 19 gave the titl e compound as a colourless gum.

$^1$H NMR (250 MHz, $CDCl_3$) δ (ppm): 6.63 (s, 1H), 6.54 (s, 1H), 4.75 (t, 1H), 4.17 (dd, 1H), 3.85 (m, 1H), 3.53 (t, 2H), 2.97 and 2.96 (2xs, 6H), 2.95 (t, 2H), 2.45–2.8 (Abq, 2H).

Description 25

3-(2-Dimethylaminoethyl)-2,3,6,7-tetrahydrofuro[2,3-f]indole

This was prepared from N,N-dimethyl-2,3,6,7-tetrahydrofuro[2,3-f]indol-3-ylacetamide (D24), following the procedure of Description 9. This gave the title compound, along with some of the corresponding indole NMR).

$^1$H NMR (200 MHz, $CDCl_3$) δ (ppm): 6.54 (s, 1H), 6.45 (s, 1H), 4.51 (t, 1H), 4.09 (dd, 1H), 3.46 (t, 2H), 3.30 (m, 2H), 2.88 (t, 2H), 2.3 (m, 2H), 2.16 (s, 6H), 1.85 (m, 1H), 1.65 (m, 1H).

Description 26

4'-Amino-2'-methylbiphenyl4-carboxylic acid

4-Bromo-3-methylaniline (7.40 g, 40 mmol) and 4-carboxybenzeneboronic acid (7.90 g, 48 mmol) were stirred in 1,2-dimethoxyethane (DME) (150 ml). Anhydrous sodium carbonate (19.0 g, 179 mmol) was dissolved in water (150 ml) and added to the above. The mixture was then purged with a stream of Ar for 15 min. Tetrakis(triphenylphosphine)palladium (O) (0.25 g, 0.2 mmol) was added, and the mixture was stirred at reflux for 20 h under Ar. DME was removed by evaporation under reduced pressure, and the clear residue was acidified (5M HCl) to yield a thick grey suspension. The solid was filtered off, washed with water and dried in vacuo at 60° C., to give the title compound (9.60 g, quantitative).

$^1$H NMR (250 MHz, d$^6$ DMSO) δ (ppm): 8.02 (d, 2H), 7.47 (d, 2H), 7.30 (d, 1H), 2H), 2.24 (s, 3H).

Description 27

Methyl 4'-amino-2'-methylbiphenyl4-carboxylate

Thionyl chloride (10 ml) was added dropwise and cautiously to methanol (200 ml) with stirring. 4'-Amino-2'-methylbiphenyl-4-carboxylic acid (D26) (8.44 g, 37 mmol) was added, and the mixture was then stirred at reflux for 3 h. Solvent was then removed in vacuo to yield the title compound (9.16 g, 89%) as the hydrochloride salt.

$^1$H NMR (HCl salt) (200 MHz, d$^6$ DMSO/$CDCl_3$) δ (ppm): 10.25 (b), 8.06 (d, 2H), 7.41 (d, 2H), 7.30 (m, 3H), 3.92 (s, 3H), 2.28 (s, 3H).

Description 28

Methyl 4'-((4-chlorobutanoyl)amino)-2'-methylbiphenyl4-carboxylate

Methyl 4'-amino-2'-methylbiphenyl-4-carboxylate (D27) (1.84 g, 7.6 mmol) and triethylamine (2.6 ml, 19 mmol) were stirred in dichloromethane (100 ml) as 4-chlorobutyryl chloride (0.94 ml, 8.4 mmol) was added dropwise. The mixture was stirred for 1 h, vigorously stirred with water for 15 min, acidified (5M HCl), and separated. The organic phase was washed with water and $K_2CO_3$/brine solution, dried ($Na_2SO_4$) and evaporated to give a light yellow solid. Chromatography on silica gel, eluting with 0–40% ether/dichloromethane, gave the title compound (1.08 g, 41%) as a light yellow solid.

$^1$H NMR (250 MHz, $CDCl_3$) δ (ppm): 8.08 (d, 2H), 7.3–7.5 (m, 5H), 7.18 (d, 1H), 3.95 (s, 3H), 3.69 (t, 2H), 2.60 (t, 2H), 2.15–2.3 (m, 5H).

Description 29

Methyl 2'-methyl4'-(2-oxo-1-pyrrolidinyl)biphenyl-4-carboxylate

Methyl 4'-((4-chlorobutanoyl)amino)-2'-methylbiphenyl-4-carboxylate (D28) (1.65 g, 4.8 mmol) was stirred in dry dimethylformamide (DMF) (20 ml) as potassium t-butoxide (0.70 g, 5.7 mmol) was added. The mixture was stirred for 30 min, diluted with ethyl acetate (200 ml), washed successively with brine, water and brine, dried ($Na_2SO_4$) and evaporated to give a light brown gum. Chromatography on silica gel, eluting with 0–50% ether/dichloromethane, gave the title compound (1.15 g, 71%) as a light yellow solid.

$^1$H NMR (250 MHz, $CDCl_3$) δ (ppm) 8.08 (d, 2H), 7.57 (d, 1H), 7.49 (dd, 1H), 7.38 (d, 2H), 7.23 (d, 1H), 3.95 (s, 3H), 3.91 (t, 2H), 2.64 (t, 2H), 2.29 (s, 3H), 2.20 (quintet, 2H).

EXAMPLE 1

4-(2-Dimethylaminoethyl)-2,3,6,7,8,9-hexahydro-6-{2'-methyl-4'-(5-methyl-1,2,4-oxadiazol-3-yl)biphenyl4-arbonyl}-4H-pyrido[2,3-g][1,4]benzoxazine 2'-Methyl-4'-(5-methyl-1,2,4-oxadiazol-3-yl)biphenyl-4-carboxlic acid (EP-0533268-A1, 0.35 g, 1.2 nunol) was stirred at reflux under Ar in thionyl chloride (10 ml) for 0.5 h, cooled, evaporated to dryness, and dissolved in dichloromethane (10 ml). This was added to a solution of 4-(2-dimethylaminoethyl)-2,3,6,7,8,9-hexahydro-4H-pyrido[2,3-g][1,4]benzoxazine (D5, 0.29 g, 1.1 mmol) and triethylamine (0.30 ml, 0.22 mol) in dichloromethane (20 ml). The mixture was stirred for 1 h, left to stand for 16 h, washed with sodium carbonate solution, dried ($Na_2SO_4$) and evaporated to a dark oil. Chromatography on silica gel, eluting with 5% methanol/dichloromethane, gave the title compound (0.20 g, 38%) as an off-white foam. The hydrochloride salt precipitated from acetone/ether.

$^1$H NMR (hydrochloride salt, 200 MHz, d$^6$DMSO) δ: 7.9 (m, 2H), 7.4 (m, 5H), 6.56 (s, 1H), 6.25 (b, 1H), 4.13 (m, 2H), 3.76 (t, 2H), 3.21(m, 2H), 3.12 (m, 2H), 3.12 (m, 2H), 3.02 (m, 2H), 2.7 (m, 11H), 2.30 (s, 3H), 1.94 (m, 2H).

EXAMPLE 2

2-(N,N-Dimethyl-3,4,6,7,8,9-hexahydro-6-[2-methyl-4'-(5'-methyl-1,2,4-oxadiazoyl-3-yl)biphenyl-4-carbonyl]-2H-pyrano[2,3-g]quinolin-4-yl)ethanamine This was prepared from 2-(N,N-dimethyl-3,4,6,7,8,9-hexahydro-2H-pyrano[2,3-g]quinolin-4-yl)ethanamine (D11), following the procedure of Example 1. This gave the title compound (56%) as a semi-solid, which was converted to its oxalate salt, a light yellow solid.

$^1$H NMR (250 MHz, d$^6$DMSO) δ (ppm): 7.95 (s, 1H), 7.90 (d, 1H), 7.4 (m, 5H), 6.8 (b, 1H), 6.61 (s, 1H), 4.07 (bs, 2H), 3.75 (m, 2H), 3.03 (t, 2H), 2.74 (t, 2H), 2.55–2.7 (s, 3H, s, 6H+1H), 2.30 (s, 3H), 1.92 (m, 3H), 1.67 (m, 3H).

EXAMPLE 3

2-(N,N-Dimethyl-2,3,5,6,7,8-hexahydro-5-[2'-methyl-4'-(5-methyl-1,2,4-oxadiazol-3-yl)biphenyl-4-carbonyl]furo[2,3-g]quinolin-3-yl)ethanamine This was prepared from 3-(2-dimethylamino)-2,3,5,6,7,8-hexahydrofuro[2,3-g]quinoline (D16), following the procedure of Example 1. This gave the title compound (41%), which was converted to its oxalate salt, an off-white solid.

$^1$H NMR (oxalate salt) (400 MHz, d$^6$DMSO) δ (ppm): 7.92 (s, 1H), 7.87 (d, 1H), 7.43 (d, 2H), 7.38 (m, 3H), 6.86 (s, 1H), 6.63 (s, 1H), 4.52 (t, 1H), 4.16 (dd, 1H), 3.75 (t, 2H), 3.27 (m, 1H), 2.88 (m, 1H), 2.82 (m, 1H), 2.76 (t, 2H), 2.66 (s, 3H), 2.59 (s, 6H) 2.30 (s, 3H), 1.94 (t, 2H), 1.76 (m, 1H), 1.68 (m, 1H).

EXAMPLE 4

4-(2-Dimethylaminoethyl)-2,3,4,6,7,8-hexahydro-6-[2'-methyl4'-(5-methyl-1,2,4-oxadiazol-3-yl) biphenyl-4-carbonyl]pyrrolo[2,3-g][1,4]benzoxazine This was prepared from 8-(2-dimethylaminoethyl)-2,3,4,6,7,8-hexahydropyrrolo[2,3-g][1,4]benzoxazine (D19), following the procedure of Example 1. This gave the title compound (15%).

$^1$H NMR (200 MHz, CDCl$_3$) δ (ppm): 8.02 (s, 1H), 7.95 (d, 1H), 7.54 (d, 2H), 7.43 (d, 2H), 7.38 (m, 2H), 6.67 (s, 1H), 4.22 (m, 2H), 4.07 (m, 2H), 3.68 (m, 6H), 3.4 (m, 2H), 3.02 (t, 2H), 2.68 (s, 4H), 2.42 (s, 3H), 2.35 (s, 3H).

EXAMPLE 5

3-(2-Dimethylaminoethyl)-5-[2'-methyl-4'-(5-methyl-1,2,4-oxadiazol-3-yl)biphenyl-4-carbonyl]-2,3,6,7-tetrahydrofuro[2,3-f]indole This was prepared from 3-(2-dimethylamino)-2,3,6,7-tetrahydrofuro[2,3-f]indole (D25), following the procedure of Example 1. This gave the title compound (27%) as a white solid. The oxalate salt crystallised from acetone.

$^1$H NMR (oxalate salt) (270 MHz, d$^6$DMSO) δ (ppm): 7.97 (s, 1H), 7.89 (d, 1H), 7.82 (b, 1H), 7.65 (d, 2H), 7.48 (d, 2H), 7.41 (d, 1H), 6.72 (s, 1H), 4.60 (t, 1H), 4.27 (dd, 1), 4.06 (t, 2H), 3.49 (m, 1H), 3.05 (t, 2H), 3.0 (m, 2H), 2.71 (s, 6H), 2.65 (s, 3H), 2.35 (s, 3H), 2.05 (m, 1H), 1.87 (m, 1H).

EXAMPLE 6

4-(2-Dimethylaminoethyl)-2,3,6,7,8,9-hexahydro-6-[2'-methyl4'-(2-oxopyrrolidin-1-yl)biphenyl-4-carbonyl]-4H-pyrido[2,3-g][1,4]benzoxazine A stirred solution of 4-(2-dimethylaminoethyl)-2,3,6,7,8,9-hexahydro-4H-pyrido[2,3-g][1,4]benzoxazine (D5, 130 mg, 0.49 mmole) in toluene (4 ml) under argon was treated with trimethylaluminium (0.27 ml of 2M in toluene, 0.54 mmole) and stirred for 20 mins. Methyl 2'-methyl4'-(2-oxo-1-pyrrolidinyl)biphenyl-4-carboxylate (D29, 154 mg, 0.50 mmole) was added and the mixture heated at 80–85° C. for 6 h, then further trimethylaluminium (0.45 ml) was added and the mixture heated under reflux for 6 h. The reaction mixture was allowed to cool, poured into a slurry of silica gel (4 g) in dichloromethane (10 ml), then loaded onto a chromatography column and eluted with 0–16% methanol/dichloromethane. The product obtained was further purified by prep. plate TLC on silica gel eluting with 10% methanol/dichloromethane to afford the title compound as a light green semi-solid (16 mg). This was converted to it hydrochloride salt as a pale yellow solid.

$^1$H NMR (free base) (250 MHz, CDCl$_3$) δ: 7.55–7.47 (m, 2H), 7.43 (d, 2H), 7.25–7.15 (m, 3H), 6.56 (s, 1H), 6.13 (br s, 1H), 4.20–4.10 (m, 2H), 3.95–3.84 (m, 4H), 3.30–3.22 (m, 2H), 3.05–2.87 (m, 2H), 2.73 (t, 2H), 2.63 (t, 2H), 2.35–2.10 (m, 11H), 2.07–1.95 (m, 2H).

I claim:

1. A compound of formula (I) or a salt or N-oxide thereof:

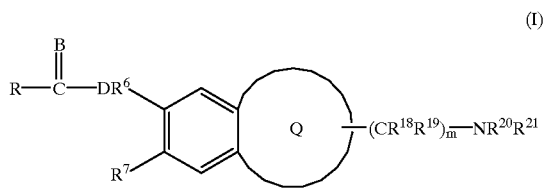

(I)

in which

R is a group of formula (i):

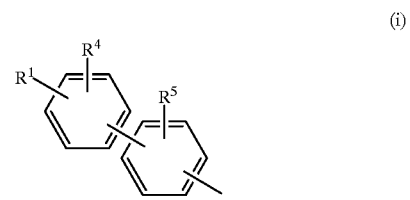

(i)

where

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, NR$^9$CONR$^{10}$R$^{11}$, NR$^{10}$SO$_2$R$^{11}$, SO$_2$NR$^{10}$R$^{11}$, CO$_2$R$^{10}$, CONR$^{10}$R$^{11}$, CO$_2$NR$^{10}$R$^{11}$, CONR$^{10}$(CH$_2$)$_a$CO$_2$R$^{11}$, (CH$_2$)$_a$NR$^{10}$R$^{11}$, (CH$_2$)$_a$CONR$^{10}$R$^{11}$, (CH$_2$)$_a$NR$^{10}$COR$^{11}$, (CH$_2$)$_a$CO$_2$C$_{1-6}$alkyl, CO$_2$(CH$_2$)$_a$OR$^{10}$, NR$^{10}$R$^{11}$, C=CNR$^9$NR$^{10}$R$^{11}$, CNR$^{10}$=NOR$^{11}$, where R$^9$, R$^{10}$ and R$^{11}$ are independently hydrogen or C$_{1-6}$alkYl and a is 1 to 4; or R$^1$ is a group —X—R$^{12}$ where R$^{12}$ is an optionally substituted 5- to 7-membered heterocyclic ring containing 1 to 4 heteroatoms selected from oxygen, nitrogen or sulphur and X is a bond, O, S, CH$_2$, C=O, NR$^{13}$CO or NR$^{13}$ where R$^{13}$ is hydrogen or C$_{1-6}$alkyl;

R$^4$ and R$^5$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are independently hydrogen or $C_{1-6}$alkyl, or $R^4$ and $R^5$ together form a group $-(CH_2)_r-R^{14}-(CH_2)_s-$ where $R^{14}$ is O, S, $CH_2$ or $NR^{15}$ where $R^{15}$ is hydrogen or $C_{1-6}$alkyl and r and s are independently 0, 1 or 2;

or R is a group of formula (ii):

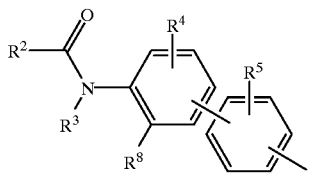

where
$R^2$ is hydrogen, $C_{1-6}$alkyl, optionally substituted aryl or optionally substituted heteroaryl;
$R^3$ is hydrogen or $C_{1-6}$alkyl or together with $R^8$ forms a group $(CH_2)_q$ where q is 2, 3 or 4;

or R is a group of formula (iii):

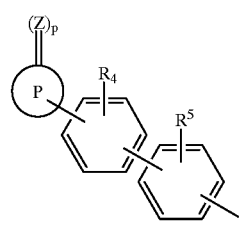

where Z is oxygen or sulphur;
p is 1 or 2;
P is an optionally substituted bicyclic ring optionally containing one to four heteroatoms;
or P is an optionally substituted 5- to 7-membered saturated or partially saturated ring optionally containing one to three heteroatoms; and
$R^4$ and $R^5$ are as defined in formula (i);
B is oxygen or sulphur;
D is nitrogen, carbon or a CH group;
$R^6$ is hydrogen or $C_{1-6}$alkyl and $R^7$ is $C_{1-6}$alkyl, $C_{1-6}$alkoxy or halogen, or $R^6$ together with $R^7$ forms a group $-A-$ where A is $(CR^{16}R^7)_t$ where t is 1, 2 or 3 and $R^{16}$ and $R^{17}$ are independently hydrogen or $C_{1-6}$alkyl or A is $(CR^{16}R^{17})_u-J$ where u is 0, 1 or 2 and J is oxygen, sulphur, $CR^{16}=CR^{17}$, $CR^{16}=N$, $CR^{16}NR^{17}$ or $N=N$;
$R^{18}$ and $R^{19}$ are independently hydrogen or $C_{1-6}$alkyl;
$R^{20}$ and $R^{21}$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur;
m is 0 to 4; and Q is an optionally substituted 5 to 7-membered heterocyclic ring containing 1 to 3 heteroatoms selected from oxygen, nitrogen or sulphur.

2. A compound according to claim 1 in which R is a group of formula (i).

3. A compound according to claim 1 in which $R^4$ is $C_{1-6}$alkyl.

4. A compound according to claim 1 in which $R^5$ is hydrogen.

5. A compound according to claim 1 in which m is 2.

6. A compound according to claim 1 in which B is oxygen and D is nitrogen.

7. A compound according to claim 1 selected from: 4-(2-Dimethylaminoethyl)-2,3,6,7,8,9-hexahydro-6-{2'-methyl-4'-(5-methyl-1,2,4-oxadiazol-3-yl)biphenyl-4-carbonyl}-4H-pyrido[2,3-g][1,4]benzoxazine, 2-(N,N-Dimethyl-3,4,6,7,8,9-hexahydro-6-[2'-methyl4'-(5-methyl-1,2,4-oxadiazol-3-yl)biphenyl-4-carbonyl]-2H-pyrano[2,3-g]quinolin-4-yl)ethanamine, 2-(N,N-Dimethyl-2,3,5,6,7,8-hexahydro-5-[2'-methyl-4'-(5-methyl-1,2,4-oxadiazol-3-yl)biphenyl4-carbonyl]furo[2,3-g]quinolin-3-yl)ethanamine, 4-(2-Dimethylaminoethyl)-2,3,4,6,7,8-hexahydro-6-[2'-methyl4'-(5-methyl-1,2,4-oxadiazol-3-yl)biphenyl4-carbonyl]pyrrolo[2,3-g][1,4]benzoxazine, 3-(2-Dimethylaminoethyl)-5-[2'-methyl-4'-(5-methyl-1,2,4-oxadiazol-3-yl)biphenyl4-carbonyl]-2,3,6,7-tetrahydrofuro[2,3-f]indole, 4-(2-Dimethylaminoethyl)-2,3,6,7,8,9-hexahydro-6-[2'-methyl4'-(2-oxopyrrolidin-1-yl)biphenyl-4-carbonyl]4H-pyrido[2,3-g][1,4]benzoxazine, or a pharmaceutically acceptable salt thereof.

8. A process for the preparation of a compound of formula (I) which comprises:
(a) for compounds of formula (I) where D is nitrogen and B is oxygen, reaction of a compound of formula (II):

in which R is as as defined in formula (I), B is oxygen and L is a leaving group with a compound of formula (III):

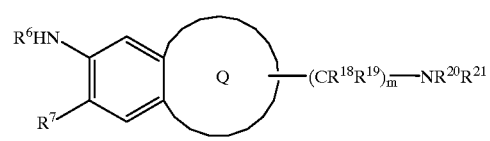

wherein $R^6$, $R^7$, $R^{18}$, $R^{19}$, $R^{20}$, $R^{21}$, Q and m are as defined in formula (I) and optionally thereafter in any order:
converting a compound of formula (I) into another compound of formula (I)
forming a pharmaceutically acceptable salt.

9. A pharmaceutical composition which comprises a compound according to claims 1 in association with a pharmaceutically acceptable carrier or excipient.

10. A method of antagonizing the $5HT_{1D}$ receptor in a subject which comprises administering an effective amount of a compound of formula (I) as described in claim 1.

11. A method of treating depression, seasonal effective disorder, dysthymia, anxiety, panic disorder, agoraphobia, social phobia, obsessive compulsive disorder, post-traumatic stress disorder, dementia, age-associated memory impairment, anorexia nervosa, bulimia nervosa Parkinson's disease, dementia in Parkinson's disease, neuroleptic-induced Parkinsonism, tardive dyskinesias which method involves treating a patient in need thereof with a therapeutically effective amount of a compound of formula (I) as described in claim 1.

12. A method of treating hyperprolactinaemia, vasospasm, hypertension and sexual dysfunction which method involves treating a patient in need thereof with a therapeutically effective amount of a compound of formula (I) as described in claim 1.

* * * * *